United States Patent [19]

Petersen et al.

[11] Patent Number: 5,133,760
[45] Date of Patent: * Jul. 28, 1992

[54] UNIVERSAL MODULAR PROSTHESIS STEM EXTENSION

[75] Inventors: Thomas D. Petersen, San Diego, Calif.; Douglas W. Stuart, Indianapolis, Ind.

[73] Assignee: Alvarado Orthopedic Research, Inc., San Diego, Calif.

[*] Notice: The portion of the term of this patent subsequent to Jan. 15, 2008 has been disclaimed.

[21] Appl. No.: 478,466

[22] Filed: Feb. 12, 1990

[51] Int. Cl.$^5$ ............................................. A61F 2/38
[52] U.S. Cl. ....................................... 623/20; 623/16
[58] Field of Search ..................... 623/16, 18, 20, 21, 623/22, 23

[56] References Cited

U.S. PATENT DOCUMENTS

| | | | |
|---|---|---|---|
| 4,462,120 | 7/1984 | Rambert et al. | 623/20 |
| 4,714,475 | 12/1987 | Grundei et al. | 623/20 |
| 4,963,155 | 10/1990 | Lazzeri et al. | 623/23 |
| 4,985,037 | 1/1991 | Petersen | 623/16 X |

FOREIGN PATENT DOCUMENTS

| | | | |
|---|---|---|---|
| 0000549 | 2/1979 | European Pat. Off. | 623/18 |
| 3535158 | 4/1987 | Fed. Rep. of Germany | 623/22 |

Primary Examiner—David Isabella
Assistant Examiner—Elizabeth M. Burke
Attorney, Agent, or Firm—H. Jay Spiegel

[57] ABSTRACT

Disclosed is an improved universal modular prosthetic stem extension which may be installed on a prosthesis in a multiplicity of differing orientations to allow adaptation to a multiplicity of differing patient conditions. The stem includes a coupling mechanism allowing the stem to be rotated to any one of a multiplicity of rotative positions with respect to a prosthetic base, whereupon the stem may be tightened and fixed in position at a desired such orientation. The inventive stem extension is disclosed in conjunction with embodiments of distal femoral, proximal tibial, and proximal femoral prostheses.

29 Claims, 7 Drawing Sheets

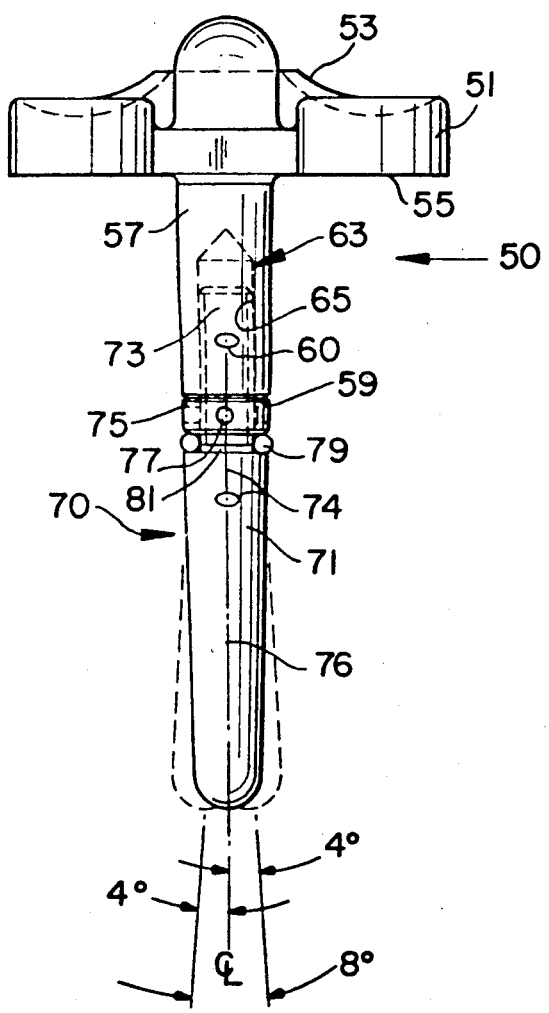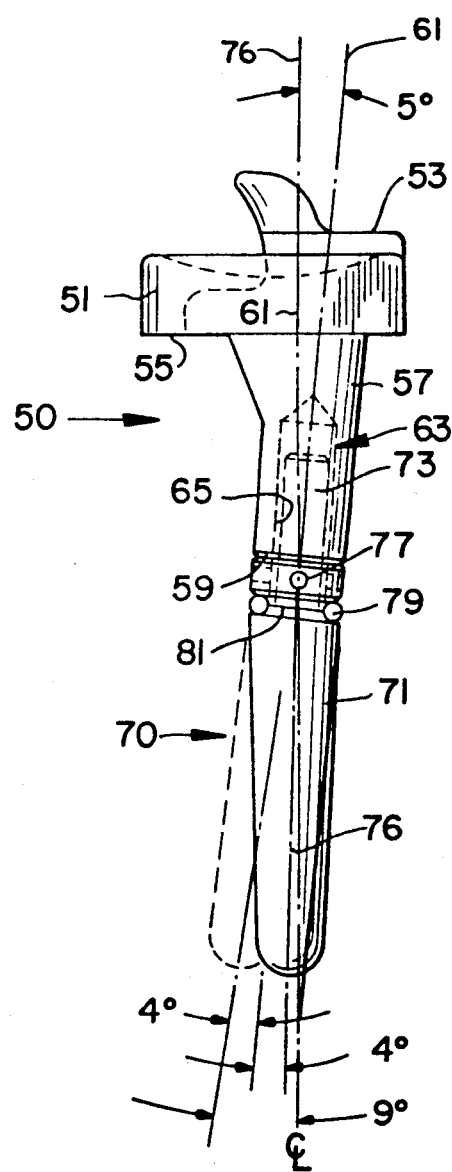

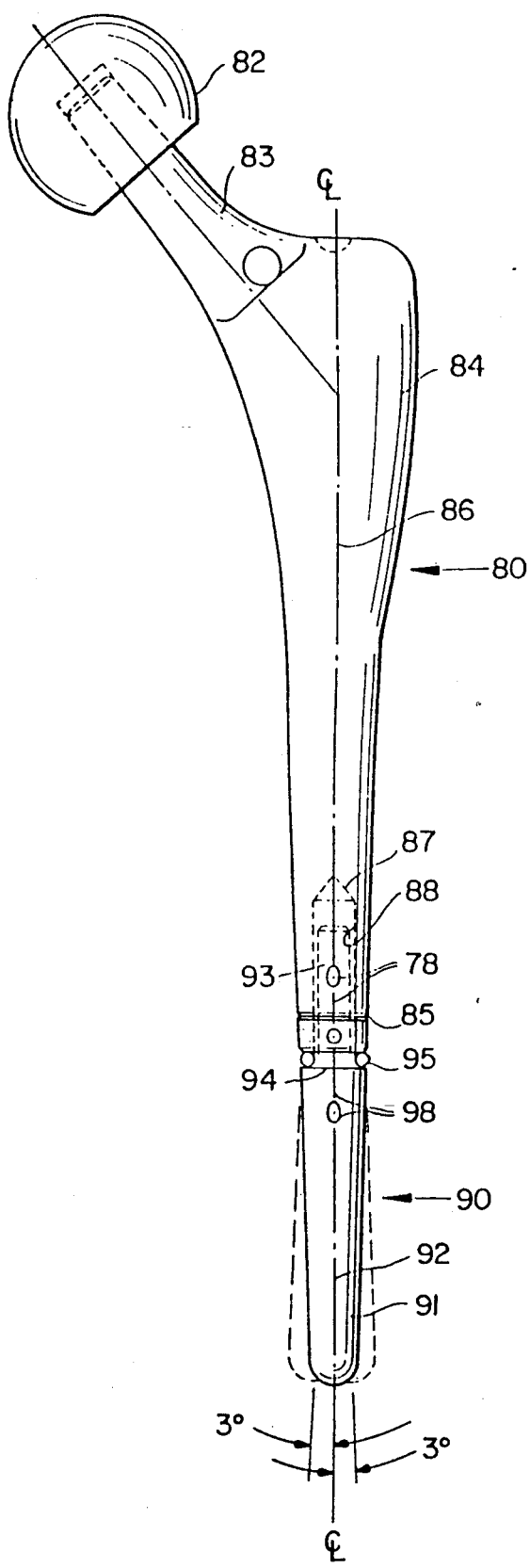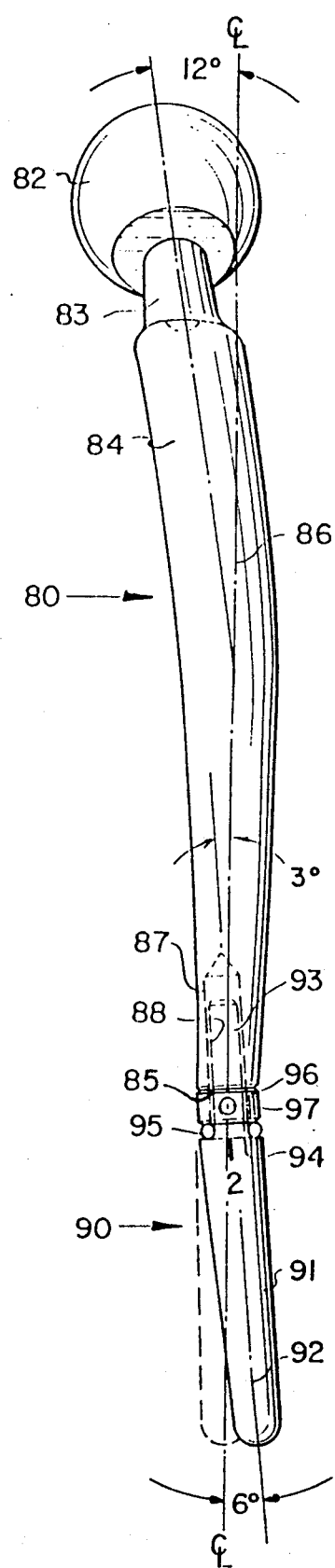

FIG. 12
FIG. 13
FIG. 14
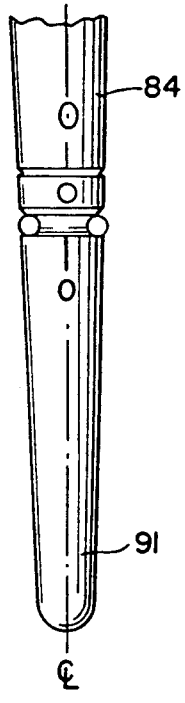
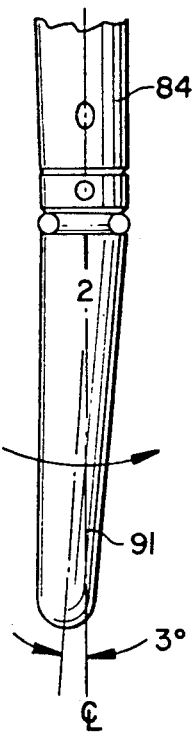
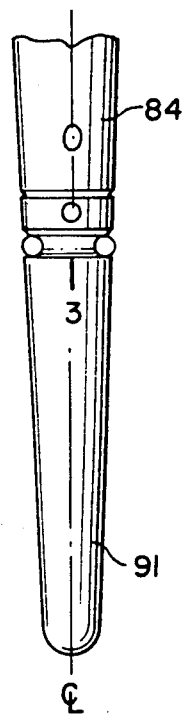
FIG. 15
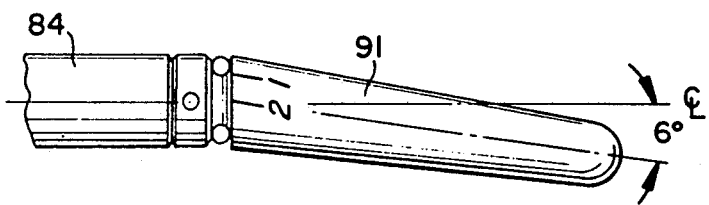
FIG. 16
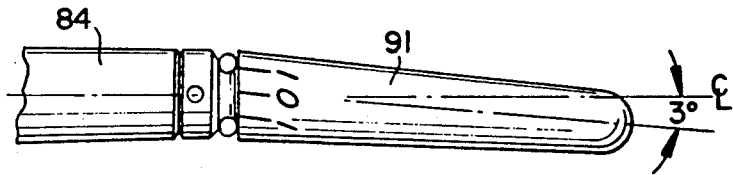
FIG. 17
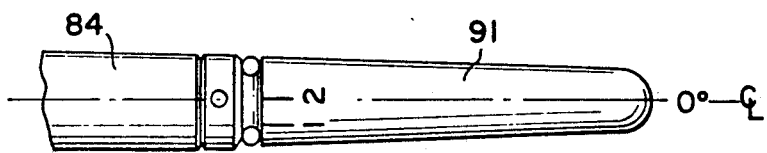

UNIVERSAL MODULAR PROSTHESIS STEM EXTENSION

BACKGROUND OF THE INVENTION

The present invention relates to embodiments of an improved universal modular prosthesis stem extension. The inventive stem extension constitutes an improvement over an invention disclosed in U.S. Pat. No. 4,985,037 in the name of coinventor Thomas D. Petersen, M.D. The entirety of the above-mentioned pending United States Patent Application is hereby incorporated by reference herein, including the discussion of prior art contained therein.

In the field of orthopedics, a definite clinical need exists for improved stem extensions for both femora and tibial components. Each year, more and more failed primary total knee and hip arthoplasties exist due to loosening, wear, or other reasons. When a total knee or hip arthoplasty fails, removal of the primary components thereof is necessitated, which commonly results in considerable bone loss necessitating a stem fixation in the subsequent implant.

Clinical experience has shown that large stem extensions act to stabilize the prosthesis through transmission of surface stresses to the stem and consequently to the cortical bone, thereby stress shielding deficient bone from torsional stresses in the immediate surface bearing area. Consequently, as surgical procedures evolve, larger and longer stems are being proposed for revision surgery.

The problem is complicated because anatomical variations in different patients require a surgeon to carry in inventory four to eight sizes of femoral components and ten to fifteen sizes of tibial components. Further complexity is added by virtue of the fact that the distal femoral stem has to be at a 5-9 degree valgus angle to the femoral components to fit the intermedullary canal of the femur. Thus, these prosthetic components require a great number of fixed stems. One manufacturer, for example, has at leas& nine different femoral stem sizes ranging from 10 millimeters to 22 millimeters in diameter. Considering the fact that they also make six femoral prostheses, for each of the left and right-hand sides, it is easy to see that over one hundred sizes and shapes of fixed prostheses have to be manufactured and must be carried in inventory by the surgeon or hospital. The high expense of each prosthesis makes carrying such a large inventory of prostheses exhorbitantly expensive.

If a stem extension could be created which could fit on the undercarriage of the articular surface of any one of a multiplicity of prostheses and, further, if such a stem extension could be designed to be adjustable to any one of a multiplicity of positions on any particular prosthesis undercarriage, the above-described inventory of prostheses could be reduced even below the six prostheses and nine reversible stem extensions to which the inventory may be reduced through the teachings of the invention disclosed in copending U.S. Patent Application Ser. No. 07/354,792.

As stated in the copending application, there are anatomical considerations in the design of a stem extension which make it desirable to have such a stem extension angled in the lateral plane as well as in the medial lateral plane. Ideally, the distal femoral cut of the femur is at 90 degrees, or perpendicular to the angular bow of the femur as seen in the lateral plane. The angle of bowing of the femur may vary from 0 up to 12 degrees; however, most femurs bow from 3 to 6 degrees. Accordingly, fitting a fixed straight stem extension into the intermedullary canal when there is significant degree of bowing may be quite difficult. However, angling of the stem extension with respect to the axis of the prosthesis facilitates more effective installation of the stem within the intermedullary canal.

As pointed out in the copending application, additional complications exist when a stem extension is included in a tibial component. As is known to those skilled in the art, some instrumentation systems which are designed to measure the exact location of tibial cuts result in cutting of the top of the tibia at varying angles such as, for example, 10 degrees, 7 degrees, 3 degrees, and some absolutely perpendicular. Thus, a properly designed stem extension could be used to modify a tibial component to the particular method of instrumentation which is utilized at minimal cost. While most surgeons use a 3-degree sloping cut on the proximal tibia, the surgical group of co-applicant Petersen has been using a 10-degree slope for a number of years and finds this slope to be advantageous in obtaining more flexion and in controlling the forward movement of the femur on the tibia when the patient is descending stairs and making other similar movements. In such a situation, of course, the prosthesis could be initially installed without the stem extension and, if a refit is necessitated, the stem extension could be easily installed.

The invention disclosed in the U.S. Pat. No. 4,985,037 constitutes a vast improvement over the prior art known at the time of the invention thereof. The invention disclosed therein contemplates providing each prosthesis which is to incorporate the inventive stem extension with an undersurface having two parallel flat walls extending upwardly from the undersurface of the prosthesis to form a generally rectangular cubic chamber therebetween. Pairs of aligned openings are formed in these walls and are designed to receive mounting pins which may also extend through holes and/or slots formed in an attachment means forming a portion of the inventive stem extension.

The attachment means of the stem extension disclosed in the copending application includes two corresponding flat parallel walls designed to slidably engage the internal surfaces of the parallel walls of the undersurface of the particular prosthesis. With this construction, this stem extension may be installed on a particular prosthesis in any one of two orientations, which orientations are rotated 180 degrees with respect to one another.

In the preferred embodiment of the stem extension disclosed in the co-pending patent application, each stem extension has a 6-degree valgus inclination as well as a degree of superior or inferior angulation such as, for example, 2 degrees. This inclination and angulation are anatomically correct in each reversed position of the modular stem extension. More particularly, the position of the stem extension, as properly mounted on a left-hand prosthesis, is anatomically correct, as is the position of the stem extension as properly mounted on a right-hand prosthesis.

While the invention disclosed in the U.S. patent is far superior to any prior designs, it is limited to only two positions of the stem extension for each prosthesis. As is known, anatomical variations of the intermedullary canals of various patients have created a need for increased versatility in prosthetic stem extensions, even over and above the versatility provided by the invention disclosed in the U.S. patent. The coupling mechanism between the stem extension and the associated undersurface of the associated prosthetic head is designed to limit the orientations of the stem extension with respect to the prosthetic undersurface to two variations spaced 180 degrees apart. If this coupling mechanism could be redesigned to provide more than two variations in orientation between the stem extension and the undersurface of the associated prosthetic head, vastly increased versatility and adaptability to differing conditions could be achieved. Also, inventories could be further reduced. It is with these thoughts in mind that the present invention was developed.

The following prior art is known to applicant:

U.S. Pat. No. 3,102,536 to Rose, et al. discloses a hip prosthesis wherein the head thereof is coupled to a neck portion of the associated stem assembly through the use of a wedging mechanism which may be loosened to allow removal of the head. The present invention differs from the teachings of Rose, et al. as allowing alterations in the orientation of a stem with respect to its associated head structure. This is not possible in the Rose, et al. device.

U.S. Pat. No. 4,687,486 to Brinckmann, et al. discloses an implant including a head coupled to a neck assembly. The device includes a nut 7 having recesses 16 designed to be engageable by a tongue 17 of a tool 15. The nut 7 is provided to allow release of separable parts of the prosthesis from one another. This is different from the teachings of the present invention, wherein, in one embodiment thereof, a nut having recesses about its periphery is utilized to tighten two components of a prosthesis in a desired orientation with respect to one another.

U.S. Pat. No. 4,693,724 to Rhenter, et al. discloses a total hip prosthesis having a stem attachable to a neck through the use of a wedged coupling. The present invention differs from the teachings of Rhenter, et al. as including structure allowing adjustment of the orientation of the stem portion thereof with a valgus inclination as well as angulations in the superior and inferior directions.

German Offenlegungsschrift 2114323 to Bostrom discloses an implantable prosthesis including a rotary joint between the stems thereof as best seen in FIG. 5 thereof. The present invention differs from the teachings of this document as including the possibility, in one embodiment thereof, of a universal joint between two portions of a stem of a prosthesis to allow adjustments in valgus inclination as well as in inclinations in the superior and inferior directions.

European Patent 0 000 549 to Seiler discloses a prosthesis including a stem having one portion implantable into the intermedullary canal and another portion having a curved neck and a head attached thereto. The other portion may be installed in the first mentioned portion in a variety of orientations in light of the coupling 12, 15, 6, 14. The present invention differs from the teachings of this document as allowing adjustments in valgus inclination as well as adjustments in angulation in the superior and inferior directions.

French Patent 2,575,383 to Lecestre, et al. discloses a prosthesis including a head attachable to a neck by virtue of a conical coupling including interrelated teeth which allow rotative adjustments between the two attached components. Lecestre, et al. do not teach or suggest adjustments in valgus inclination of a stem nor adjustments in angulation of a stem in the superior or inferior directions as taught herein.

European Patent 0 201 407 to Montagne discloses a femoral prosthesis wherein a single stem assembly may be attached to one of a plurality of heads by virtue of one of a multiplicity of stem extensions. The present invention differs from the teachings of Montagne as including different structure for the attachment of the various components together.

SUMMARY OF THE INVENTION

The present invention relates to embodiments of an improved universal modular prosthesis stem extension. The present invention includes the following interrelated aspects and features:

(a) Firstly, the inventive stem extension may be applied to any prosthesis including a distal femoral prosthesis, a proximal tibial prosthesis, and a proximal femoral prosthesis. These are merely examples of the types of prostheses to which the present invention may be applied.

(b) In each prosthesis to which the teachings of the present invention are applied, the undersurface of the prosthetic component is provided with an upstanding base extending upwardly from the undersurface a significant distance.

(c) In all embodiments of the present invention, the base includes an elongated recess which is preferably threaded. The associated stem extension has a threaded terminus which is threadably received within the threaded elongated recess.

(d) In one embodiment of the inventive stem extension, the threaded terminus has a lock nut threadably received thereon in such a manner that the stem extension may be rotated with respect to the base to any one of a variety of rotative positions with respect thereto, whereupon the lock nut may be threaded into engagement with the base to thereby lock the position of the stem extension in a desired orientation. The longitudinal axis of the main portion of the stem extension is angled to a desired degree with respect to the threaded terminus so that rotation of the threaded terminus with respect to the base results in differing orientations and angulations of the main portion of the stem extension with respect to the base of the prosthesis and the prosthesis itself.

(e) In a further embodiment of the inventive stem extension, the threaded terminus of the stem extension includes a radially outwardly extending shoulder designed to bear against the base when the threaded terminus is threaded into the elongated threaded recess thereof, with the shoulder bearing against the base to tighten the stem extension thereagainst. This shoulder may, if desired, have flats or a polygonal periphery to facilitate gripping with a tool. Proximal of the shoulder, a universal coupling is provided which connects the threaded terminus with the main portion of the stem extension. The universal coupling includes a lock nut and a split socket which interact to allow tightening and loosening of the split socket with respect to a ball forming the distal terminus of the main portion of the stem extension. By loosening the lock nut, the main portion of the stem extension may be adjusted to provide any desired valgus inclination as well as any desired angulation in the superior and inferior directions. Thereafter, the lock nut may be tightened to fix the position of the main portion of the stem extension with respect to the threaded terminus thereof as well as with respect to the base of the prosthesis and the prosthesis itself.

As such, it is a first object of the present invention to provide an improved universal modular prosthesis stem extension.

It is a further object of the present invention to provide such an invention which may be applied to various types of prostheses.

It is a yet further object of the present invention to provide such an invention including different embodiments of adjustment means allowing adjustment of the orientation of the stem extension which respect to the associated prosthesis.

These and other objects, aspects and features of the present invention will be better understood from the following detailed description of the preferred embodiments when read in conjunction with the appended drawing figures.

BRIEF DESCRIPTION OF THE DRAWINGS

FIG. 8 shows a front view of a proximal tibial prosthesis having the teachings of the present invention incorporated therewith.

FIG. 9 shows a side view of the prosthesis of FIG. 8.

FIG. 10 shows a left antero-posterior view of a proximal femoral prosthetic component having the teachings of the present invention incorporated therewith.

FIG. 11 shows a left view of the lateral side of the prosthetic component of FIG. 10.

FIGS. 12-17 show views of the stem extension of the proximal femoral prosthesis of FIGS. 10 and 11 in various adjusted positions thereof.

SPECIFIC DESCRIPTION OF THE PREFERRED EMBODIMENTS

Figure 1:
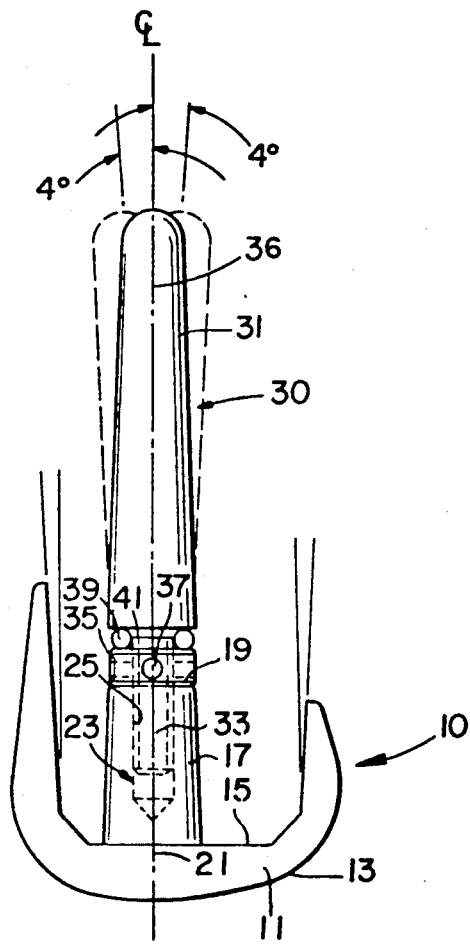
FIG. 1 shows a side view of a distal femoral prosthesis including the teachings of the present invention incorporated therewith.
Figure 2:
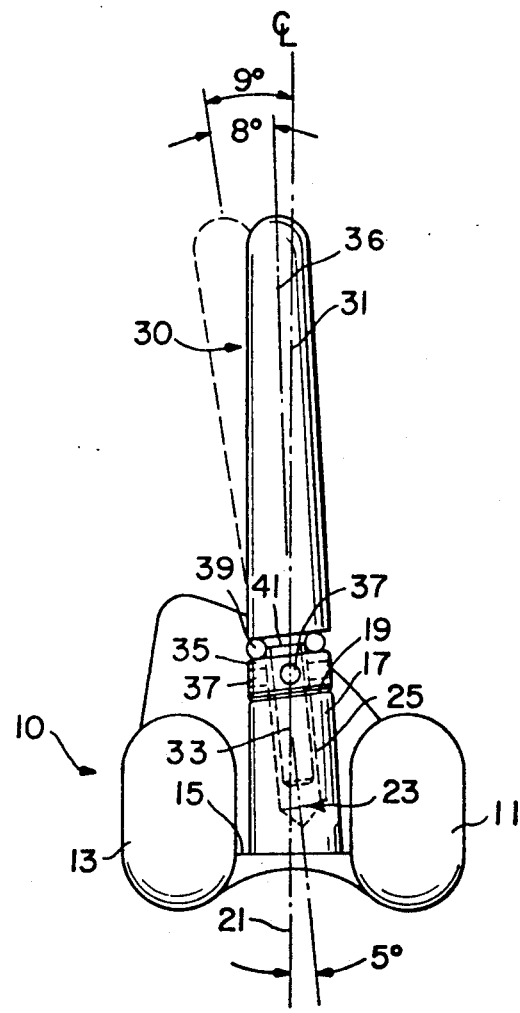
FIG. 2 shows a front view of the prosthesis of FIG. 1.
Figure 3:
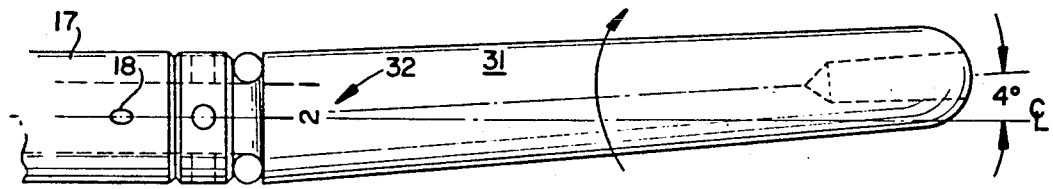
FIGS. 3-7 show the stem extension of the prosthesis of FIGS. 1 and 2 in its various positions and orientations.
Figure 4:
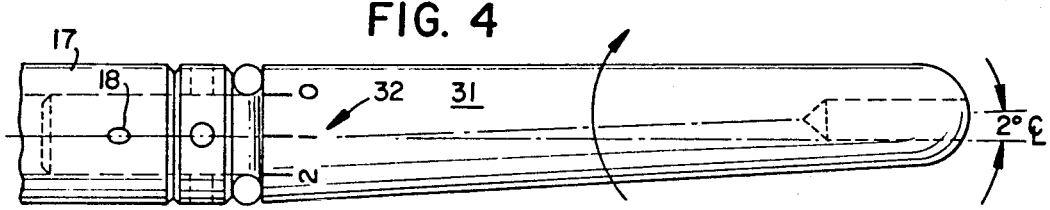
Figure 5:
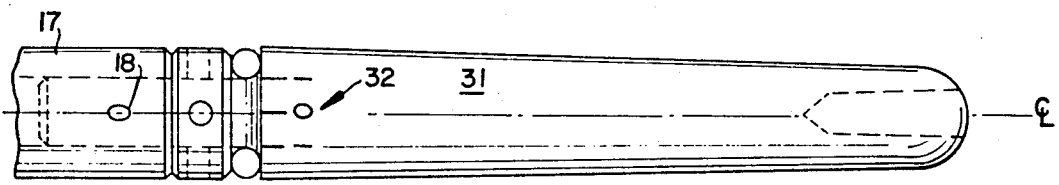
Figure 6:
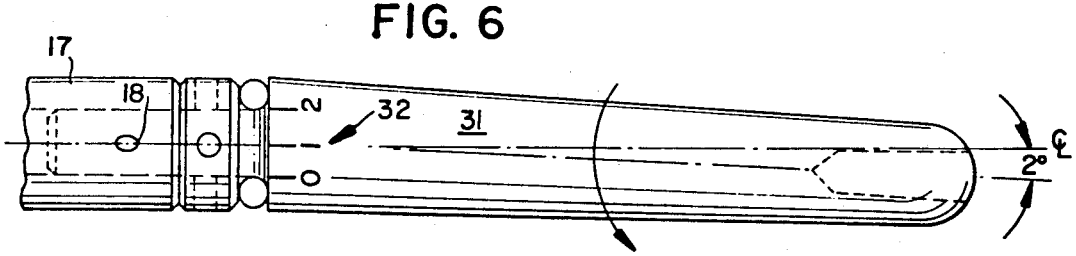
Figure 7:
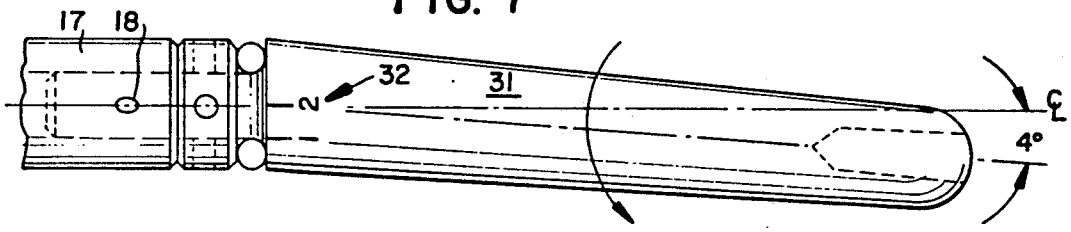

With reference, first, to FIGS. 1 and 2, a distal femoral prosthesis is generally designated by the reference numeral 10 and is seen to include a prosthetic head 11 having a bearing surface 13 as well as an undersurface 15. Upstanding from the undersurface 15 is a base 17 having a top surface shoulder 19 which is angled in the view of FIG. 2 by 5 degrees with respect to the longitudinal axis 21 of the base 17.

The base 17 includes a first mounting means consisting of a threaded recess 23 including threaded walls 25 for a purpose to be described in greater detail hereinafter.

As also seen in FIGS. 1 and 2, a stem extension 30 includes a stem portion 31 and a second mounting means consisting of a terminus 33 comprising a threaded projection which is angled approximately 8 to 9 degrees from the axis 36 of the stem, as best seen in FIG. 2. The terminus 33 is threaded in complimentary fashion to the threaded surfaces 25 of the recess 23 so that the threaded terminus 33 may be threadably received within the threaded recess 23.

Threadably received on the threaded terminus 33 is a nut 35 which may, if desired, have tool receiving recesses 37. An O-ring 39 is mounted on the threaded terminus 33 between the nut 35 and a shoulder 41 between the stem portion 31 and the threaded terminus 33. The O-ring 39 is preferably made of silicone and is provided for two reasons. Firstly, the O-ring 39 is provided for aesthetic reasons to reduce the size of the gap which is created between the nut 35 and the shoulder 41 when the nut 35 is tightened to fix the orientation of the stem portion 31 on the base 17. Secondly, when cement is used in the procedure for installing the prosthesis, this cement might migrate into this gap and might thus cause difficulty with subsequent stem removal, should removal become necessary providing the O-ring 39 in this location prevents such cement migration.

With reference to FIGS. 3-7, it is seen that the stem extension 31 includes indicia generally, designated by the reference numeral 32 in FIGS. 3-7. These indicia consist of the consecutive numerals 2, 1, 0, 1 and 2. Furthermore, the base 17 includes a zero mark indicium 18 designed to be alignable with any one of the indicia 32.

Alignment of each respective indicium 32 with the indicium 18 results in respective degrees of valgus correction and superior and/or inferior angulation of the stem portion 31 with respect to the base 17 of the prosthesis 10. These relationships are depicted in Table A as follows:

TABLE A

| | DISTAL FEMUR | | | | |
|---|---|---|---|---|---|
| Indicia | Valgus Angulation | Valgus Angulation | Resultant Valgus Angu- | SUPERIOR/INFERIOR ANGULATION | |
| PROSTHE-SIS/STEM | Fixed on Prosthesis | Variable on Stem | lation of Prosthesis/Stem Combination | SUPERIOR Clockwise Rotation | INFERIOR Counter-clockwise Rotation |
| 0/0 | 5° | 4° | 9° | 0° | 0° |
| 0/1 | 5° | 2° | 7° | 2° | 2° |
| 0/2 | 5° | 0° | 5° | 4° | 4° |

Of course, the figures included in Table A are based upon the angulations between the stem portion 31 and the threaded terminus 33, as well as in light of the angle between the axis of the threaded recess 23 and the axis of the base 17 of the prosthesis 10. These angular relationships are merely exemplary and may differ from the figures disclosed herein, should different angular relationships be appropriate.

With reference, now, to FIGS. 8 and 9, a proximal tibial prosthesis is generally designated by the reference numeral 50, and is seen to include a prosthetic head 51 having a bearing surface 53 and an under surface 55. Upstanding from the undersurface 55 of the prosthetic head 51 is a base 57 extending along an axis 61 and including a terminating shoulder 59. Zero mark indicium 60 includes a scored line extending to the shoulder 59.

The base 57 includes a recess 63 including threaded walls 65 for a purpose to be described in greater detail hereinafter.

A stem extension 70 includes a stem portion 71 and a terminus 73 having walls threaded correspondingly to the threaded wall 65 of the recess 63 so that the threaded terminus 73 may be threadably received within the threaded recess 63.

A nut 75 is threadably received on the threaded terminus 73 and, if desired, may include tool receiving recesses 77. An O-ring 79 is mounted on the threaded tarminus 73 between the nut 75 and a shoulder 81 defining the intersection of the stem portion 71 and the threaded terminus 73. Indicia 74 include scored lines extending to shoulder 81 and alignable with indicium 60 on various rotative positions of the stem 70 with respect to the base 57.

As best seen in FIG. 9, the threaded recess 63 in the base 57 is angled in the view of FIG. 9 five degrees (5°) with respect to the longitudinal axis 76 of the base 57. Furthermore, as seen in FIG. 9, the threaded terminus 73 is angled with respect to the longitudinal axis 76 of the stem portion 71 by an angle of approximately, 8 to 9 degrees.

Thus, in a manner corresponding the manner of adjustment of the stem extension 30 of FIGS. 1–7, the stem extension 70 may be adjusted with respect to the base 57 of the prosthesis 50 to align indicium 60 with one of the indicia 74 to provide variation in posterior angulation as well as variation in angulation in the medial-lateral direction. In the example shown in FIGS. 8 and 9, Table B, below, depicts the various degrees of correction in the posterior and mediallateral directions as follows:

seen in FIG. 11. Zero mark indicium 78 includes a scored line extending to shoulder 85.

The stem 84 includes a recess 87 having threaded walls 88 for a purpose to be described in greater detail hereinafter.

A stem extension 90 includes a stem portion 91 having a longitudinal axis 92, which stem portion 91 has attached thereto a terminus 93 which is threaded correspondingly to the threads of the threaded walls 88 of the recess 87 so that the threaded terminus 93 may be threadably received therein.

A shoulder 94 defines the intersection of the stem portion 91 and the threaded terminus 93. Indicia 98 include respective scored lines extending to shoulder 94.

As seen in FIGS. 10 and 11, an O-ring 95 is captured on the threaded terminus 93 by a nut 96 which is threadably received on the threaded terminus 93 and which preferably includes tool receiving recesses 97.

As best seen in FIG. 11, the stem portion 91 of the stem extension 90 is angled with respect to the threaded terminus 93 by an angle of 6 degrees. This angular relationship, combined with the angle of the shoulder 85 of the stem 84, combine to allow rotations of the stem extension 90 with respect to the stem 84 to provide different corrections in the posterior direction as well as in the medial-lateral direction. As described above, the stem portion 91 and the stem 84 have respective indicia 98, 78 corresponding to the indicia included in the embodiments described above to allow the surgeon to "dial in" the desired correction. Using these indicia, the corrections which may be dialed in by the surgeon are depicted in Table C as follows:

TABLE C

| INDICIA | | Posterior Angulation Fixed on Prosthesis | Posterior Angulation Variable on Stem | Resultant Posterior Angulation of Prosthesis/ Stem Combination | MEDIAL/LATERAL ANGULATION | | | |
|---|---|---|---|---|---|---|---|---|
| | | | | | MEDIAL | | LATERAL | |
| Prosthesis | Stem | | | | LEFT RIGHT | Rotate Clockwise Rotate Counterclockwise | LEFT RIGHT | Rotate Counterclockwise Rotate Clockwise |
| 0 | 0 | 3° | 3° | 6° | | 0° | | 0° |
| 0 | 1 | 3° | 1.5° | 4.5° | | 1.5° | | 1.5° |
| 0 | 2 | 3° | 0° | 3° | | 3° | | 3° |
| 0 | 3 | 3° | 3° | 0° | | 0° | | 0° |

Of course, the angular relationships depicted in Table C are merely exemplary and may differ from the listed figures, should different angular relationships the appropriate.

TABLE B

| INDICIA | | Posterior Angulation Fixed on Prosthesis | Posterior Angulation Variable on Stem | Resultant Posterior Angulation of Prosthesis/ Stem Combination | PROXIMAL TIBIA | | | |
|---|---|---|---|---|---|---|---|---|
| | | | | | MEDIAL/LATERAL ANGULATION | | | |
| | | | | | MEDIAL | | LATERAL | |
| Prosthesis | Stem | | | | LEFT RIGHT | Rotate Clockwise Rotate Counterclockwise | LEFT RIGHT | Rotate Counterclockwise Rotate Clockwise |
| 0 | 0 | 5° | 4° | 9° | | 0° | | 0° |
| 0 | 1 | 5° | 2° | 7° | | 2° | | 2° |
| 0 | 2 | 5° | 0° | 5° | | 4° | | 4° |

Of course, the angular relationships depicted in Table B are merely exemplary and may differ from the listed figures, should different angular relationships be appropriate.

With reference, now, to FIGS. 10 and 11, the proximal femoral prosthesis is generally designated by the reference numeral 80, and is seen to include a prosthetic head 82 attached to a neck 83 which is attached to a stem assembly 84, which terminates at a shoulder 85 angle <i with respect to the axis 86 of the stem 84 as best FIGS. 12–14 depict views of the stem extension 91 and stem 84 of a left proximal femoral stem prosthesis in the antero-posterior direction.

FIGS. 15–17 depict respective lateral views of the same structures at three respective different relationships therebetween. Comparison of FIGS. 15, 16 and 17 reveals a preferred relationship between indicia "0" and respective indicia "2" of 90° angular spacing. This, the two indicia "2" are preferably spaced 180° apart about the circumference of the stem extension 91.

Figure 20:
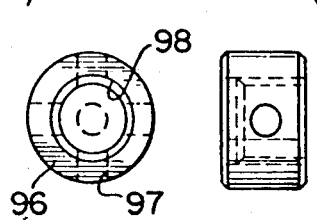
FIG. 20 shows a spanner lock nut also shown in FIGS. 18 and 19.
Figure 19:
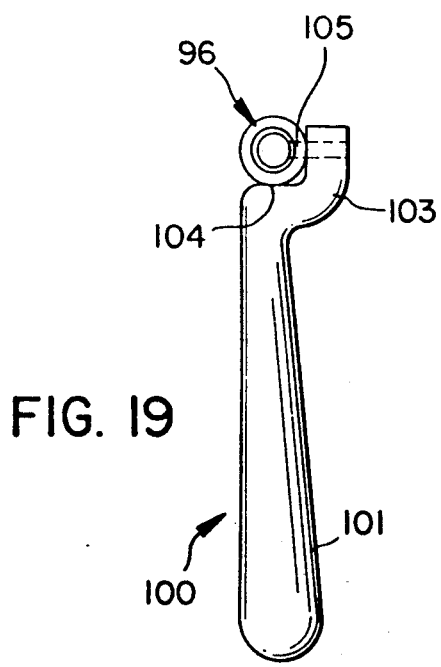
FIG. 19 shows a spanner wrench designed to be used with the embodiment illustrated in FIG. 18.
Figure 18:
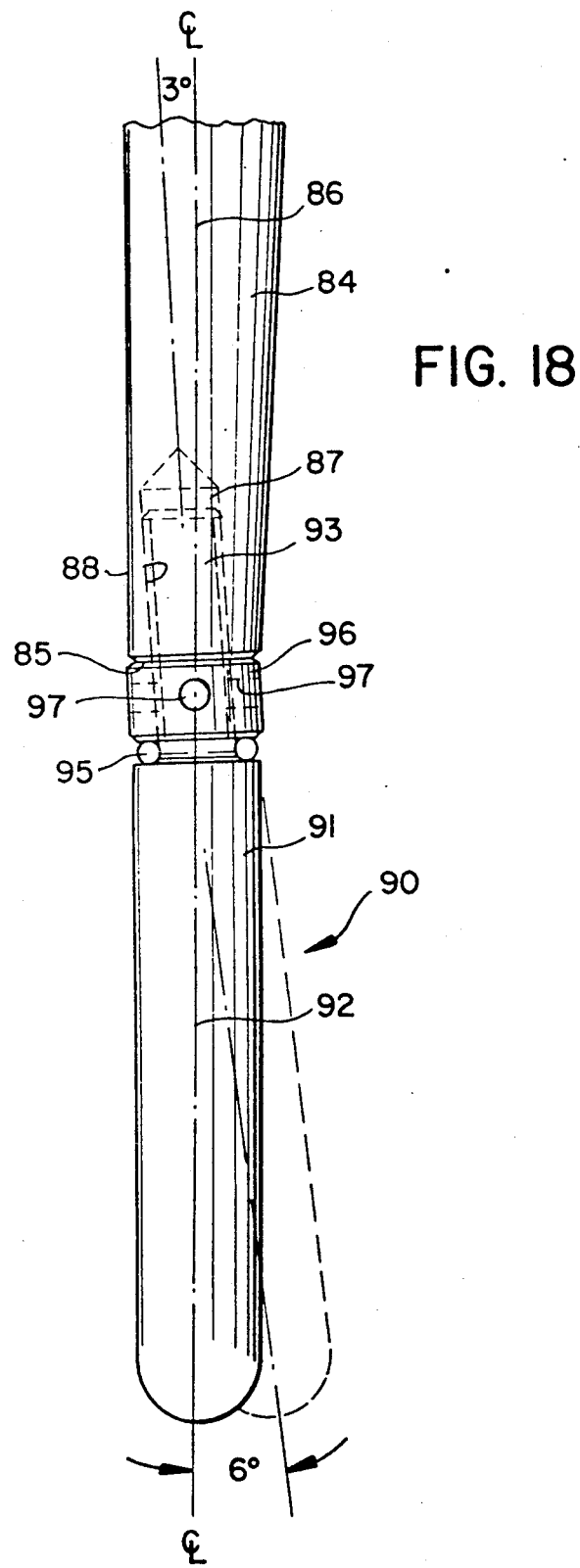
FIG. 18 shows a close-up view of the attachment of the stem extension to the rest of a prosthesis in one embodiment thereof.

With reference, now, to FIGS. 18-20, more detailed explanation of the manner of tightening of the stem extension in a desired configuration will be given. In FIG. 18, the prosthesis depicted is the same as that which is shown in FIGS. 10 and 11. However, the mode of adjustment described with reference to FIGS. 18-20 is precisely the same as that which would be employed in the embodiments of FIGS. 1-9.

With particular reference to FIG. 19, a tool 100 is provided which includes a handle 101, a head 103, a flat surface 104, and a protruding finger 105. As seen in FIG. 19, the finger 105 is sized and configured to enter one of the tool receiving recesses 97 in the nut 96, with the surface 104 of the tool 100 designed to tangentially engage a side wall of the nut 96. In such configuration, rotative movements of the tool 100 allow rotation of the nut 96 with the threaded walls 98 thereof causing the nut 96 to be advanced or retracted, as the case may be, depending upon the direction of rotation thereof. When it is desired to lock the position of the stem portion 91 with respect to the stem 84, with the rotative position of the stem portion 91 at the desired relationship to the stem 84, the nut 96 may be advanced against the shoulder 85 of the stem 84 and may be tightened there until a wedging action occurs with regard to the various threads of the recess walls 88, threaded terminus 93 and nut 96 so that locking of the position of the stem portion 91 with respect to the stem 84 is accomplished. When it is desired to adjust the position of the stem portion 91 with respect to the stem 84 or, alternatively, to remove the stem portion 91 from the stem 84, one must merely reverse the direction can rotation of the nut 96 using the tool 100 to loosen the engagement of the nut 96 from the wall 85 of the stem 84, whereupon the Stem 90 threaded terminus 93 ma be threaded out from the threaded walls 88 of the recess 87.

Figure 21:
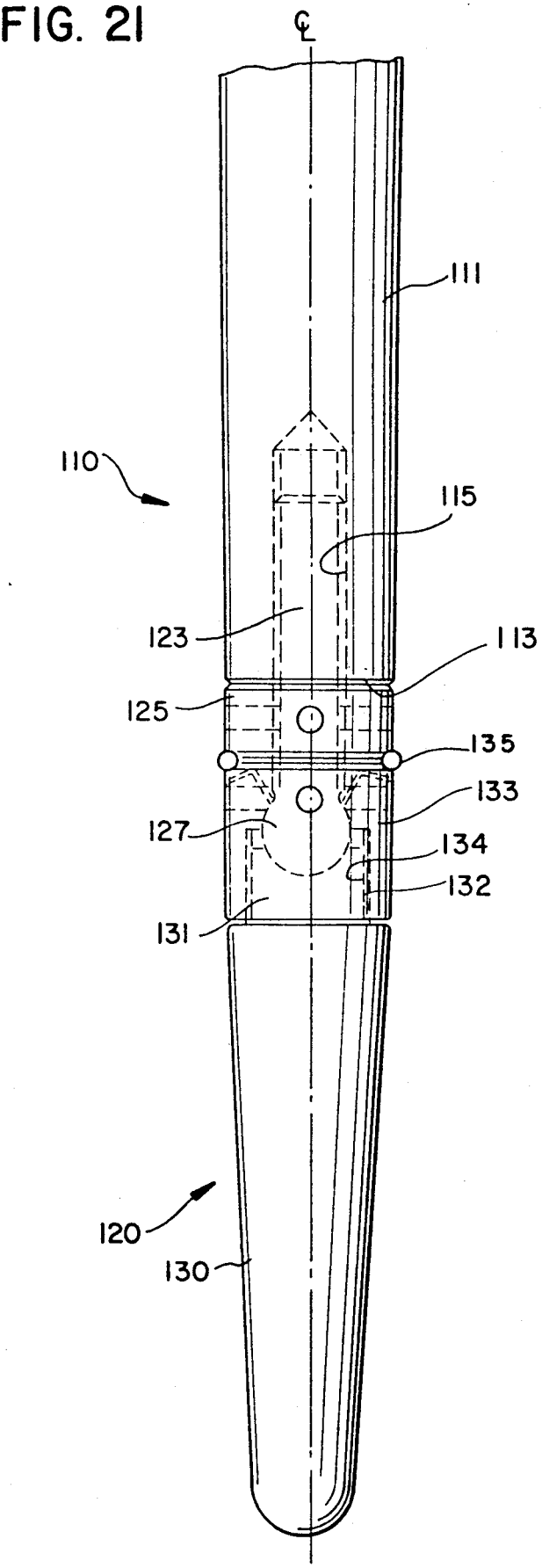
FIG. 21 shows a cross-sectional view of a further embodiment of attachment of a stem extension to a prosthesis including a universal joint.

With reference, now, to FIG. 21, a further embodiment of stem structure is generally designated by the reference numeral 110. A prosthesis includes a base 111 corresponding to the base 17 illustrated in FIGS. 1-7 and the base 57 illustrated in FIGS. 8 and 9. Thus, the base 111 protrudes upwardly from the undersurface of a prosthetic head (not shown).

The base 111 includes a terminating shoulder 113 having a threaded recess 115 therein sized and configured to receive the threaded terminus 123 of a stem extension 120. The stem extension 120 includes a nut 125 threaded on the terminus 123 and adapted to bearingly engage the shoulder 113 of the base 111 so that the threaded terminus 123 may be fixedly secured to the base 111 in a desired rotative relation with respect thereto.

The threaded terminus 123 has a proximal end to which is integrally attached a ball 127.

A stem 130 is seen to include, integrally formed therewith, a first socket half 131 adapted to engage a proximal surface of ball 127. Socket half 131 has a threaded periphery 132 and threadably receives a second socket half 133 having a complimentary internally threaded surface 134. An O-ring 135 is mounted between the second socket half 133 and the nut 125 to fill the gap therebetween and prevent cement migration.

With the socket half 133 loosened to allow the first socket half 131 to move with respect to the ball 127, the stem 130 may freely move universally in all directions so that the surgeon may adjust the angulation of the stem 130 with respect to the base 111 to any desired degree. When the desired degree of orientation of the stem 130 with respect to the base 111 has been achieved, second socket half 133 may be rotated to move downwardly the view of FIG. 21 to tighten against the ball 127 to thus tighten the socket 131, 133 about the ball 127 of the stem extension 120 to fix the position of the stem 130 in the desired configuration. If desired, indicia (not shown) may be provided between the socket 131, 133 and ball 127 to allow the surgeon to always know the orientation of the stem 130 with respect to the base 111 with the indicia indicating the degrees of displacement in the various planes such as, for example, the anteroposterior plane, the medial-lateral plane, etc. Through the use of the stem assembly depicted in FIG. 21, any desired adjustment in the position and orientation of the stem 130 with respect to the base 111 may be carried out.

Of course, if desired, other types of connection means between the stem extension and the base of the associated prosthesis may be employed. One such example is known as an angled Brown and Sharpe (Morse taper-type) connection. However, this type of connection means is not preferred because there have been some recent reports that such attachment means may come loose during use to thereby allow debris to be released into the bone tissue.

In a further aspect, the embodiments disclosed hereinabove have been disclosed in terms of specific angles of inclination in the various planes and directions. It is stressed that these disclosed angles are merely exemplary, and the inventive prostheses may be manufactured with any desired angles for any desired degree of versatility.

One example of a surgical method which may be employed in installing a prosthesis including the inventive stem extension is as follows: For example, a patient may require a total knee revision or, may be an extremely heavy patient or making it desirable to include a stem extension on the primary prosthesis. After the necessary cuts are made to accept the prosthesis and a temporary centering template is placed over the distal femur or proximal tibia, a tap is used to tap the intermedullary canal to determine the proper angulation of the stem. A trial component is then used with the attached stem in the approximate optimal position and angulation as perceived by the surgeon through use of the tap.

The trial stem is tightened using fastening means such as those disclosed in the above described embodiments and indicia on the respective adjacent structures of the stem extension and base are noted, with the respective parts being loosened and adjusted as desired until such time as the fit is as close as is possible. When the trial prosthesis and stem have been made to fit optimally within the intermedullary canal, the surgeon notes the position of the respective indicia and calls for the final prosthesis.

At this point, the permanent stem extension is inserted into the final prosthesis and the fastening means such as, for example, the nut 96, is tightened with the indicia in configuration corresponding to the indicia of the trial prosthesis. If, for some reason, the is not precise, the nut 96, for example, may be loosened so that adjustment of the orientation of the stem extension with respect to the base of the prosthesis may be made. After the final fit is obtained, the nut 96, for example, is tightened to make the configuration permanent.

As such, the present invention in terms of embodiments thereof and method of use has been disclosed which has great utility and novelty. Of course, various changes, modifications and alterations in the teachings of the present invention may be contemplated by those skilled in the art without departing from the intended spirit and scope thereof. As such, it is intended that the present invention only be limited by the terms of the appended claims.

We claim:

1. A modular prosthesis system comprising:
   a) a prosthetic head having an undersurface;
   b) head mounting means on said undersurface;
   c) a stem extension having stem mounting means for mounting said stem extension to said head mounting means in any one of a plurality of orientations with respect thereto;
   d) said stem extension having a stem portion, connected to said stem mounting means and defining an obtuse angular relationship therebetween.

2. The invention of claim 1, wherein said stem portion is connected to said stem mounting means with a valgus inclination.

3. The invention of claim 2, wherein said stem extension is reversible for installation on either a left-hand or right-hand prosthetic head.

4. The invention of claim 2, wherein said stem portion is connected to said stem mounting means with neutral angulation in a superior/inferior direction in one orientation thereof with respect to said prosthetic head.

5. The invention of claim 2, wherein said valgus inclination is 5 degrees.

6. The invention of claim 2, wherein said stem portion is connected to said stem mounting means with left inferior angulation reversible to right superior angulation in one orientation thereof with respect to said prosthetic head.

7. The invention of claim 6, wherein said left inferior angulation and right superior angulation is from 0-4 degrees.

8. The invention of claim 2, wherein said stem portion is connected to said stem mounting means with left superior angulation reversible to right inferior angulation in one orientation with respect to said prosthetic head.

9. The invention of claim 8, wherein said left superior angulation and right inferior angulation is from 0-4 degrees.

10. The invention of claim 1, wherein said stem mounting means includes an O-ring interposed between said stem mounting means and said stem portion.

11. The invention of claim 10, wherein said head mounting means comprises a threaded recess in said prosthetic head undersurface.

12. The invention of claim 11, wherein said stem mounting means comprises a threaded projection threaded complimentary to said threaded recess.

13. The invention of claim 9, further including a lock nut carried on said threaded projection and moveable to a position in engagement with a shoulder adjacent said threaded recess to lock a rotative position of said stem extension with respect to said prosthetic head.

14. The invention of claim 1, wherein said head mounting means and said stem mounting means combine to form a universal joint allowing multiple adjustment of angular relationships between said prosthetic head and stem extension.

15. The invention of claim 1, wherein said prosthetic head comprises a femoral head knee joint prosthesis.

16. The invention of claim 1, wherein each said stem portion is tapered from a larger diameter adjacent said stem mounting means to a smaller diameter terminating distally therefrom.

17. The invention of claim 16, wherein said stem extension may be oriented with respect to said prosthetic head to provide angulation with respect thereto in a medial-lateral plane.

18. The invention of claim 1, wherein said prosthetic head comprises a tibial prosthetic head for a knee joint prosthesis system.

19. The invention of claim 1, wherein said prosthetic head comprises a femoral head hip joint prosthesis.

20. The invention of claim 1, wherein said head mounting means extends away from said undersurface at an angle non-perpendicular with respect thereto.

21. The invention of claim 20, wherein said angle is approximately 85° in a lateral direction with respect to said prosthetic head.

22. The invention of claim 1, wherein said head mounting means and said stem mounting means have mutually alignable indicia means for allowing precise adjustment of a particular desired orientation of said stem extension with respect to said head to provide said prosthesis system with a desired degree of valgus correction and/or superior or inferior angulation.

23. A method of performing surgery including the steps of:
   (a) providing a modular prosthesis system comprising:
      (i) a prosthetic head having an undersurface;
      (ii) head mounting means on said undersurface;
      (iii) a stem extension having stem mounting means for mounting and locking said stem extension to said head mounting means in any one of a plurality of orientations with respect thereto;
      (iv) said stem extension having a stem portion connected to said stem mounting means and defining an obtuse angular relationship therebetween;
      (v) said prosthetic head and stem extension combining to comprise a prosthesis;
   (b) surgically preparing a bone to accept said prosthetic head and stem extension;
   (c) adjusting the orientation of said stem extension with respect to said prosthetic head to render said prosthesis compatible with said surgically prepared bone;
   (d) locking said orientation between said stem extension and said prosthetic head; and
   (e) surgically fastening said prosthesis to said bone.

24. The method of claim 23, further including the step of employing said stem extension with either a right-hand prosthesis or a left-hand prosthesis.

25. The method of claim 23, wherein said adjusting step is employed to adjust valgus inclination of said stem extension with respect to said prosthetic head.

26. The method of claim 23, wherein said adjusting step is employed to adjust superior/inferior angulation of said stem extension with respect to said prosthetic head.

27. The method of claim 23, wherein said adjusting step is employed to adjust posterior angulation of said stem extension with respect to said prosthetic head.

28. The method of claim 23, wherein said adjusting step is employed to adjust medial/lateral angulation of said stem extension with respect to said prosthetic head.

29. The method of claim 28, further including the step of, during said adjusting step, aligning an indicium on said head with an indicium on said stem extension to provide said prosthesis system with a desired degree of valgus correction and/or superior or inferior angulation.

* * * * *